United States Patent [19]

Sullivan et al.

[11] Patent Number: 4,653,644
[45] Date of Patent: Mar. 31, 1987

[54] PACKAGE FOR TOXIC FUMIGANT MATERIAL IN PELLET OR TABLET FORM AND METHOD OF MAKING SAME

[75] Inventors: Jeremiah B. Sullivan; Donald G. Shaheen, both of Harrisonburg; Richard P. Stanovick; Robert L. Dove, both of Weyers Cave, all of Va.

[73] Assignee: DEGESCH GmbH, Frankfurt am Main, Fed. Rep. of Germany

[21] Appl. No.: 621,761

[22] Filed: Jun. 18, 1984

[51] Int. Cl.[4] ............................................. B65D 83/04
[52] U.S. Cl. ..................................... 206/538; 206/0.5; 206/539; 239/60
[58] Field of Search ...................... 206/213.1, 0.5, 538, 206/539; 239/60

[56] References Cited

U.S. PATENT DOCUMENTS

| | | |
|---|---|---|
| 3,311,229 | 3/1967 | Troll et al. ............................ 206/539 |
| 3,866,347 | 2/1975 | Schoom . |
| 4,040,515 | 8/1977 | Hessel et al. .......................... 206/0.5 |
| 4,101,711 | 7/1978 | Stillman ............................... 206/484 |
| 4,215,508 | 8/1980 | Allen et al. ........................... 206/0.5 |
| 4,444,310 | 4/1984 | Odell .................................. 206/539 |

FOREIGN PATENT DOCUMENTS

| | | |
|---|---|---|
| 20103 | 4/1967 | Australia . |
| 1531677 | 5/1967 | France . |
| PCT/DE/79- 00061 | 10/1979 | PCT Int'l Appl. . |
| 2022420 | 12/1979 | United Kingdom . |

Primary Examiner—William T. Dixson, Jr.
Assistant Examiner—Brenda J. Ehrhardt
Attorney, Agent, or Firm—Cushman, Darby & Cushman

[57] ABSTRACT

A package for the application of a fumigant material includes a first sheet having a plurality of recesses for receiving a fumigant in pellet or tablet form in each recess and a second sheet one side of which is coated with an adhesive which is applied over the openings and surrounding surface area of the first sheet and adhered thereto by heat and pressure; the material of the sheet is a spun bonded polyester which permits ingress of moisture containing atmosphere. The release of the toxic gas produced by the moisture induced decomposition of the pellets takes place at a much higher effective rate than has been the case with previous packages for similar material.

17 Claims, 4 Drawing Figures

U.S. Patent   Mar. 31, 1987   4,653,644
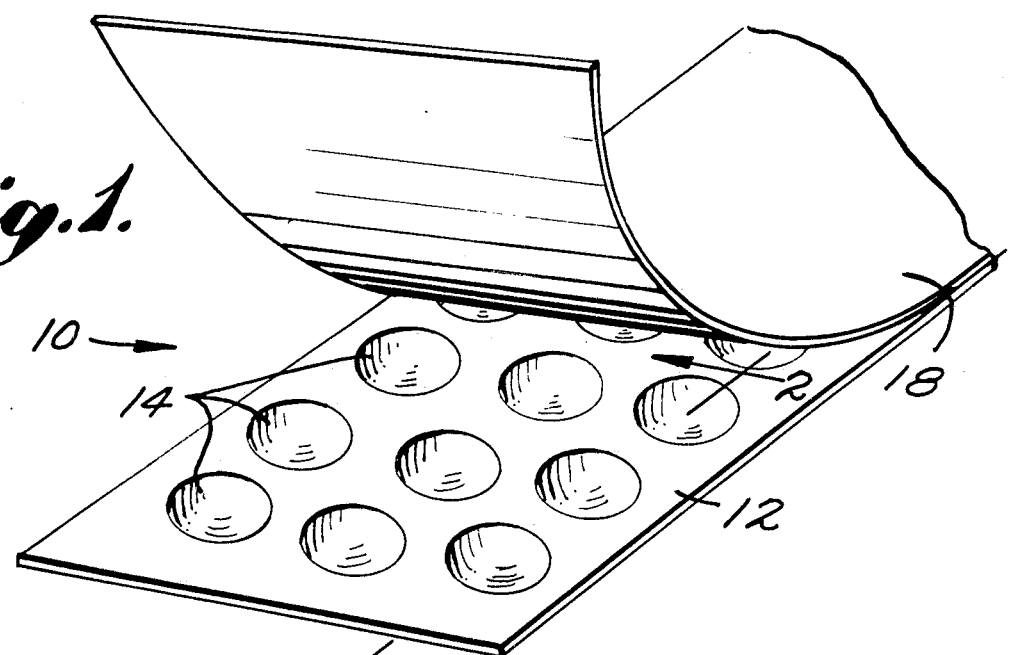
Fig. 1.
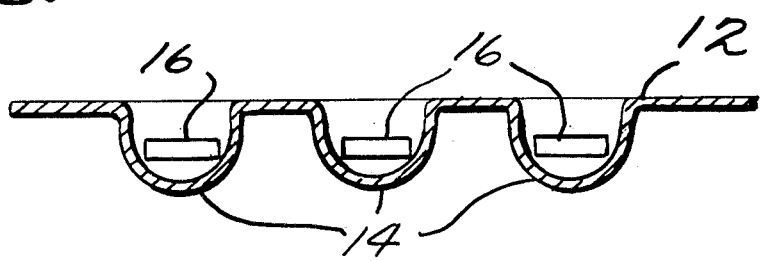
Fig. 2.
Fig. 3.
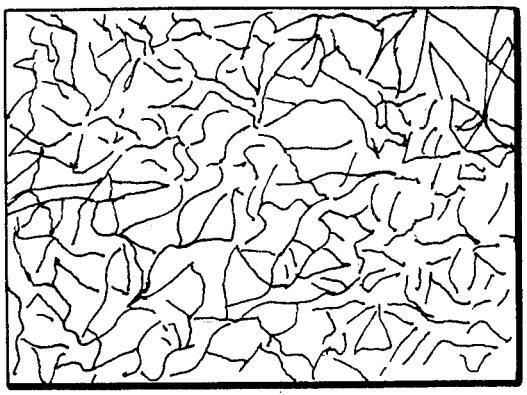
Fig. 4.
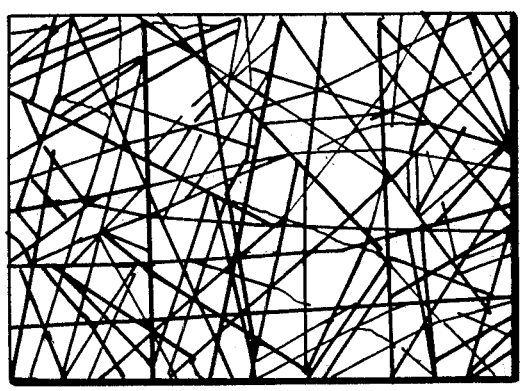

PACKAGE FOR TOXIC FUMIGANT MATERIAL IN PELLET OR TABLET FORM AND METHOD OF MAKING SAME

BACKGROUND AND SUMMARY OF THE INVENTION

The present invention relates to application packages for fumigant material such as aluminum phosphide and magnesium phosphide both of which are available in tablet or pellet form and which decompose upon contact with moisture in the atmosphere to form a toxic gas.

As is well known, the handling of pesticides, particularly those that result in the production of a toxic gas, are dangerous and require extreme care in handling and applying the pesticide to an area where one desires to eliminate rodent and insect parasites. Specifically, with the use of aluminum phosphide or magnesium phosphide such as that disclosed in U.S. Pat. No. 3,888,347 and which is assigned to the same assignee as the present application, it is important to avoid physical contact with the fumigant material itself. To this end, various types of mechanical applicators have been employed in the past to disperse the fumigants in pellet or tablet form throughout a locality or area. These specific fumigants decompose upon exposure to moisture in the atmosphere and generate a toxic gas which, if properly confined in an area, will effectively eliminate any pests and then dissipate to the atmosphere or break down into non-toxic products without leaving any harmful residue.

Due to the foregoing properties, it is obviously important that the pellets or tablets, once distributed, uniformly decompose to provide the required concentration of gas in an area and, that the decomposition period be relatively short to permit use of the product under various time, temperature and humidity conditions.

Previous application packages for these fumigants have required extensive periods for sufficient decomposition of the pellets or tablets to take place and therefore have resulted in undesirable delays in workers gaining access to the area that has been fumigated.

According to the present invention, it has now been found that a spun-bonded synthetic filament sheet can be used as the packaging material. More specifically, where the synthetic filament is a polyester and where the sheets, constructed according to a known process, are made with an average weight per unit of area of approximately 100 grams per square meter ($g/m^2$), the best results are obtained in terms of decomposition time and package strength, tear resistance and handling and storage characteristics. The characteristic of polyester fibers, that they can be heat set in a specific configuration, makes this fiber very suitable for this type of packaging.

In addition to the foregoing advantages, other advantages will become apparent as consideration is given to the following detailed description taken in conjunction with the accompanying drawings, in which:

BRIEF SUMMARY OF THE DRAWINGS

FIG. 1 is a perspective view of one end of a package of the present invention;

FIG. 2 is a view along lines 2—2 of FIG. 1;

FIG. 3 is a magnified view of the fibers of one of the sheet of the package of the present invention; and FIG. 4 is a view similar to FIG. 3 but showing another orientation of the fibers used in the sheet material of the package of the present invention.

DETAILED DESCRIPTION OF THE INVENTION

As is well known, pesticides that leave harmful residues such as ethylene dibromide, can no longer be safely used due to the toxic materials that appear in the food chain. It is, therefore, highly desirable that other fumigants such as magnesium phosphide and aluminum phosphide be used so long as these materials can be safely applied to an area it is desired to fumigate.

Referring now to the drawings, wherein like numerals designate corresponding parts, there is shown a package 10 of the present invention which will greatly facilitate the application of these fumigants in pellet or tablet form to a locality while avoiding hazardous contact by workers (and the commodity to be fumigated) with the toxic material. To this end, the present invention utilizes spun-bonded synthetic filament sheets and, more specifically, spun-bonded polyester filament sheets to form the package 10.

In constructing the package, a first sheet 12 which has previously been formed with a plurality of hemispherical indentations or recesses 14, may be passed beneath an automatic dispensing machine so that a tablet 16 will be deposited in each of the recesses 14 of the sheet 12. Subsequently, a second sheet 18 of spun-bonded polyester filament, which has previoulsy been coated with a polyethylene powder as an adhesive is placed over the flat surface of the sheet 12 and bonded thereto by the application of heat and pressure. This may be accomplished by passing the package 10 with the two sheets in juxtaposition and with the lower sheet located in a perforated screen whereby the recesses 14 may protrude through the recesses, beneath a heated pressure plate to effect the adhesive bonding of the sheet 18 to the flat surface area of sheet 12.

The materials for the sheets 12 and 18 are available from the Dupont Company and sold under the trademark "REEMAY". As shown in Dupont Technical Bulletin S-13 of August 1974, which is incorporated herein by reference, the "REEMAY" sheets are made from a continuous-filament polyester fiber that are randomly arranged and highly dispersed and bonded at the filament junctions. The sheets may be made with crimped fibers which, with a 50X magnification will appear as shown in FIG. 3 while the sheets made with the straight fibers, with a similar degree of magnification will appear as shown in FIG. 4.

Preferably, sheet 12 should be that sold under the style number 2295 and which has a unit weight of 100 $g/m^2$ while the sheet 18 is preferably that sold under the style number 2414 which has a unit weight of 34 $g/m^2$.

TABLE NO. 1

| | Hydrogen Phosphide Gas Evolution Rates | | | | |
|---|---|---|---|---|---|
| | Exposure Conditions | | Times to 10, 50 and 90% Decomposition | | |
| Products | Temp. (°C.) | R.H. (%) | $T_{10}$ (hrs) | $T_{50}$ (hrs) | $T_{90}$ (hrs) |
| Aluminum Phosphide Tablets | 20–22 | 85–95 | 4.8 | 13.9 | 24.6 |
| Aluminum Phosphide Pellets | 20–22 | 85–95 | 4.1 | 10.9 | 19.2 |
| Aluminum Phosphide Prior Art Pack. | 20–22 | 85–95 | 4.5 | 16.6 | 34.9 |

TABLE NO. 1-continued

| | Hydrogen Phosphide Gas Evolution Rates | | | | |
|---|---|---|---|---|---|
| | Exposure Conditions | | Times to 10, 50 and 90% Decomposition | | |
| Products | Temp. (°C.) | R.H. (%) | $T_{10}$ (hrs) | $T_{50}$ (hrs) | $T_{90}$ (hrs) |
| Mag. Phosphide Tablets | 20–22 | 85–95 | 1.5 | 7.5 | 18.0 |
| Mag. Phosphide Pellets | 20–22 | 85–95 | 1.5 | 6.2 | 12.2 |
| Mag. Phosphide Magtoxin Pellets Package of Spun-Bonded Polyester | 20–22 | 85–95 | 0.4 | 2.5 | 6.0 |

With reference now to Table 1, it will be seen that aluminum phosphide tablets when simply exposed to the atmosphere at the stated exposure conditions take just over 24 hours to decompose by 90% whereas under the same stated exposure condition when enclosed in a prior art package, the aluminum phosphide pellets required almost 35 hours to decompose by 90%. The magnesium phosphide pellets under the stated exposure conditions normally require 12 hours to decompose 90% without any package. However, with the package of the spun-bonded polyester of the present invention, the pellets only required only 6 hours to decompose by 90%. With, of course, lower relative humidity, decomposition times would be longer for both aluminum phosphide as well as magnesium phosphide, as is expected.

TABLE NO. 2

| | Residual Metal Phosphide Levels in Partially Spent Fumigants Exposed at High Humidity | | | |
|---|---|---|---|---|
| | Residual Metal Phosphide Conc (% Metal Phosphide) | | | |
| Exposure Period (hrs) | Mag. Phosphide Tablet Prior Package | Modified Mag. Phosphide Pellet Package | Mag. Phosphide Tablets | Mag. Phosphide Pellets |
| 0 | 66.0 | 66.0 | 66.0 | 66.0 |
| 19 | 10.4 | 1.0 | 3.7 | 0.6 |
| 27.5 | 0.9 | 0.7 | 1.2 | 0.7 |

The residual metal phosphide levels in partially spent fumigants is shown in Table 2. The modified magnesium phosphide pellet package is the package of the present invention.

TABLE NO. 3

| | Residual Metal Phosphide Levels in Partially Spent Fumigants Exposed at Low Humidity | | | |
|---|---|---|---|---|
| | Residual Metal Phosphide Conc (% Metal Phosphide) | | | |
| Exposure Period (hrs) | Mag. Phosphide Tablet Prior Package | Modified Mag. Phosphide Pellet Package | Mag. Phosphide Tablets | Mag. Phosphide Pellets |
| 0 | 66.0 | 66.0 | 66.0 | 66.0 |
| 14 | — | 28.4 | — | 28.3 |
| 19 | 47.5 | 9.6 | 47.5 | 24.3 |
| 22 | — | 0.8 | 36.6 | 24.4, 23.1 |

Table 3 shows the residual metal phosphide levels at low humidity conditions. The data clearly establishes that the packaging of the pellets in the spun-bonded polyester aids in the degassing of the magnesium phosphide. This will greatly facilitate the use of this fumigant without regard to temperature or relative humidity.

Having described the invention, it will be apparent that modifications may be made thereto without departing from the spirit and scope of this invention as defined in the appended claims.

What is claimed is:

1. A method of packaging fumigant material that is provided in a discrete pellet or tablet form, comprising the steps of:
    selecting a first sheet of spun-bonded synthetic filament material having a plurality of recesses protruding from one side of said sheet, the size of each said recess being sufficient to completely receive a pellet or tablet therein, said recesses being spaced from one another, said sheet having a flat surface area on a side thereof opposite the side from which said recesses extend;
    supplying a discrete pellet or tablet of fumigant material to each said recess;
    selecting a second sheet of spun-bonded polyester filament fibers having a surface for bonding to said flat surface area of said first sheet, one of said surfaces of said second sheet and said flat surface area of said first sheet having an adhesive material thereon; and
    applying pressure and heat to bond said sheets together.

2. The method as claimed in claim 1 including the step of selecting said sheets with different weight per unit area.

3. The method of claim 2 wherein said first sheet has a weight per unit area of approximately 100 g/m$^2$.

4. The method of claim 3 wherein said second sheet has a weight per unit area of approximately 34 g/m$^2$.

5. The method as claimed in claim 1 including the step of heating said sheets when applying said pressure.

6. The method as claimed in claim 1 including the step of applying said adhesive to said surface of said second sheet.

7. The method as claimed in claim 6 including the step of using, as the adhesive, polyethylene powder.

8. The method as claimed in claim 1 including the step of supplying at least pellets or tablets to each said recess.

9. A package for discrete pellets or tablets of a fumigant material of the type that decomposes upon exposure to moisture and which produces a toxic gas upon decomposition, comprising:
    a first sheet of spun-bonded synthetic filaments having formed therein spaced apart recesses protruding from one side of said sheet;
    a second flat sheet of spun-bonded polyester filaments adhesively secured to the side opposite said one side of said first sheet with each said recess including a discrete pellet of fumigant material therein.

10. The packages as claimed in claim 9 wherein an adhesive is applied to one side of said second sheet.

11. The package as claimed in claim 10 wherein said adhesive is polyethylene powder.

12. The package as claimed in claim 9 wherein said first sheet has a weight of approximately 100 g/m$^2$.

13. The package as claimed in claim 9 wherein said second sheet has a weight of approximately 34 g/m$^2$.

14. The package as claimed in claim 9 wherein said first sheet is approximately 18 mils thick.

15. The package as claimed in claim 9 wherein said second sheet is approximately 8 mils thick.

16. The package as claimed in claim 14 wherein said second sheet is approximately 8 mils thick.

17. The package as claimed in claim 9 wherein said recesses are substantially uniformly spaced from one another on said first sheet.

* * * * *